United States Patent [19]

Barrut

[11] Patent Number: 4,478,580

[45] Date of Patent: Oct. 23, 1984

[54] PROCESS AND APPARATUS FOR TREATING TEETH

[76] Inventor: Luc P. Barrut, 14 Rue Robert, Lyon 6eme - Rhone, France

[21] Appl. No.: 463,369

[22] Filed: Feb. 3, 1983

[30] Foreign Application Priority Data

Feb. 5, 1982 [DE] Fed. Rep. of Germany ....... 3203937

[51] Int. Cl.³ .............................................. A61L 11/00
[52] U.S. Cl. .................................................. 433/223
[58] Field of Search ............... 433/223, 215, 218, 219, 433/76

[56] References Cited

U.S. PATENT DOCUMENTS

| | | | |
|---|---|---|---|
| 3,861,044 | 1/1975 | Swinson | 433/218 |
| 4,182,312 | 1/1980 | Mushabac | 433/68 |
| 4,324,546 | 4/1982 | Heitlinger | 433/213 |
| 4,411,626 | 10/1983 | Becker et al. | 433/223 |

FOREIGN PATENT DOCUMENTS 40165 11/1981 European Pat. Off. ............ 433/223

*Primary Examiner*—Robert Peshock
*Attorney, Agent, or Firm*—Remy J. VanOphem

[57] ABSTRACT

A process and apparatus for treating a tooth. A probing device probes the contours of the tooth while generating signals corresponding to both the position of the probing device and the pressure between the probing device and the tooth so as to generate an accurate indication of the contours of the tooth. A data processing device processes the signals and produces control signals for controlling various tools for machining or otherwise producing orthodontic appliances, particularly crowns.

32 Claims, 48 Drawing Figures

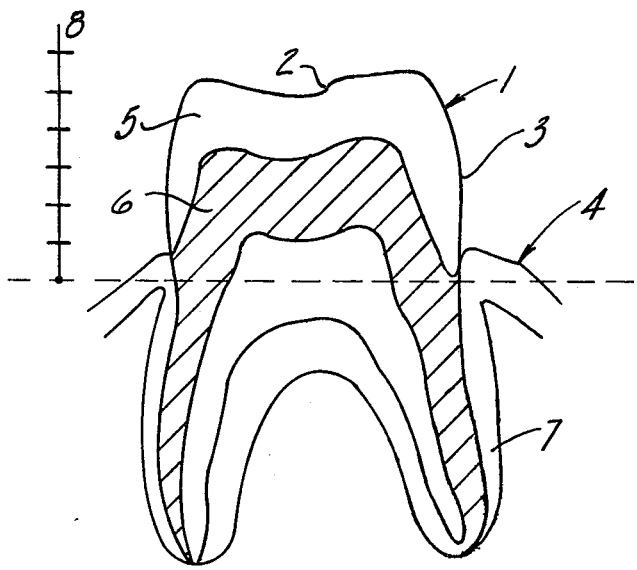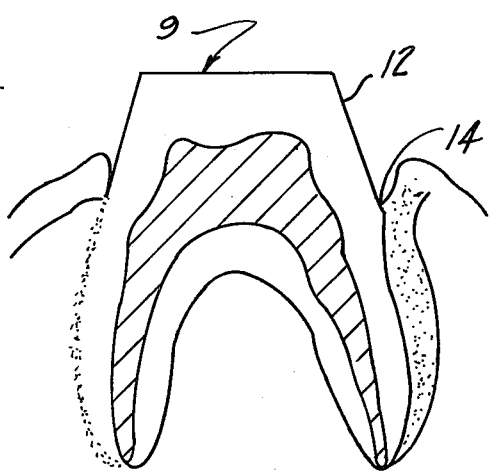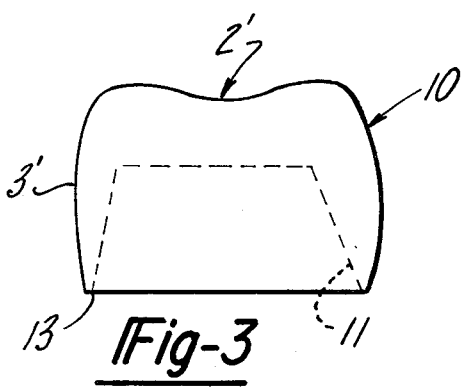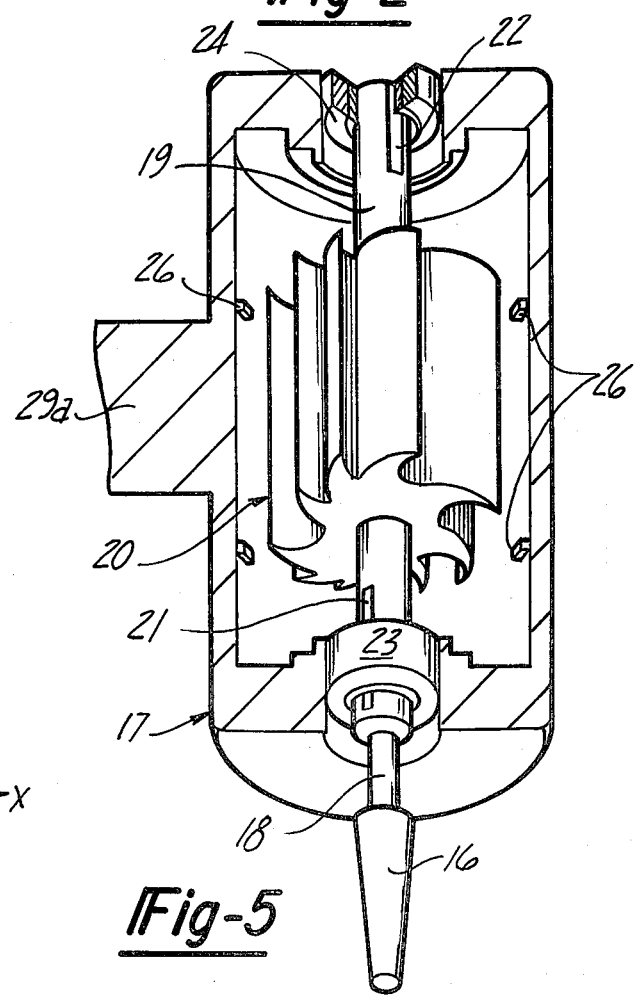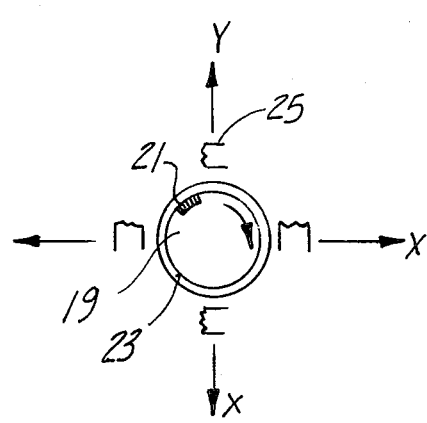
Fig-1
Fig-2
Fig-3
Fig-5
Fig-6

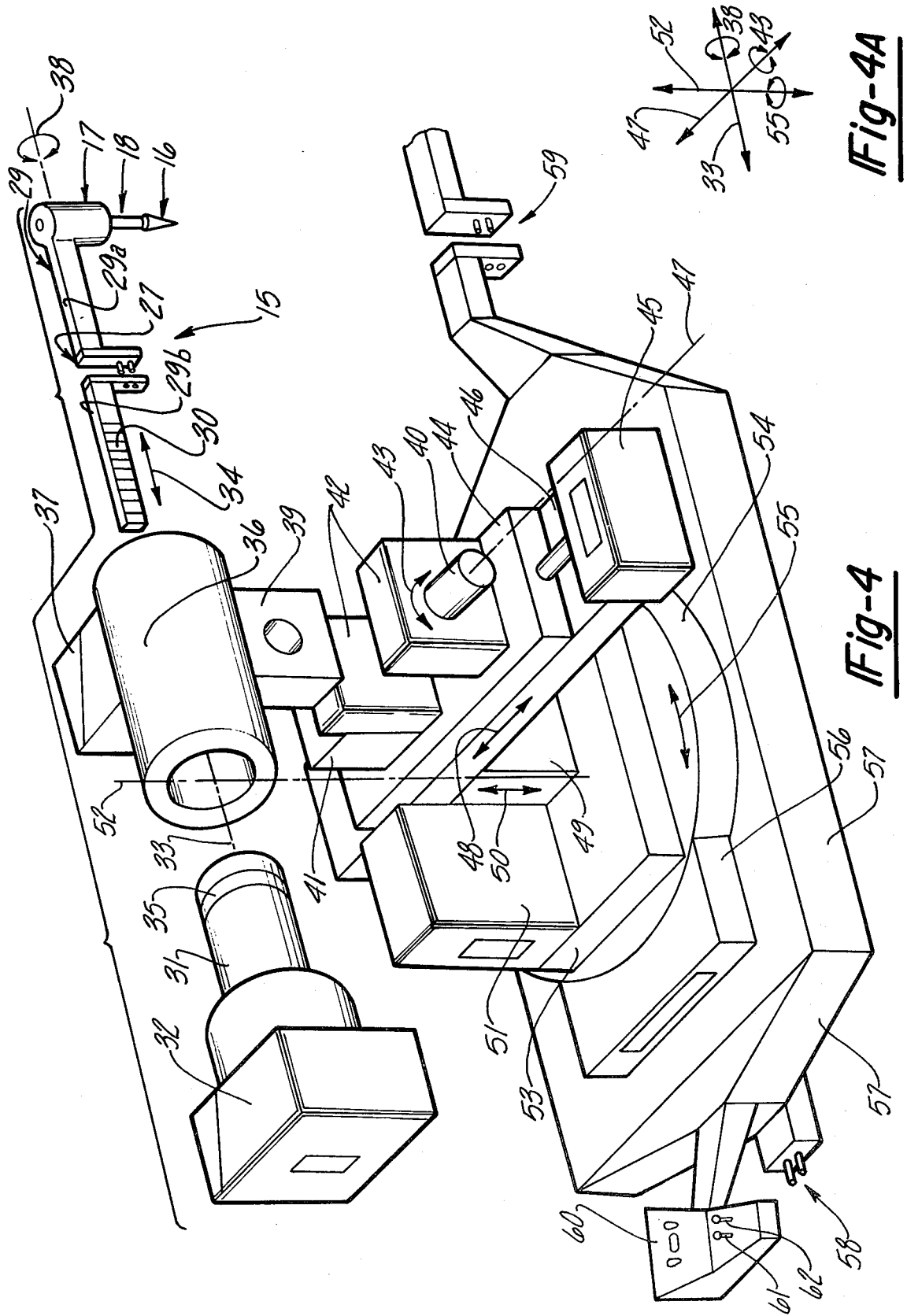

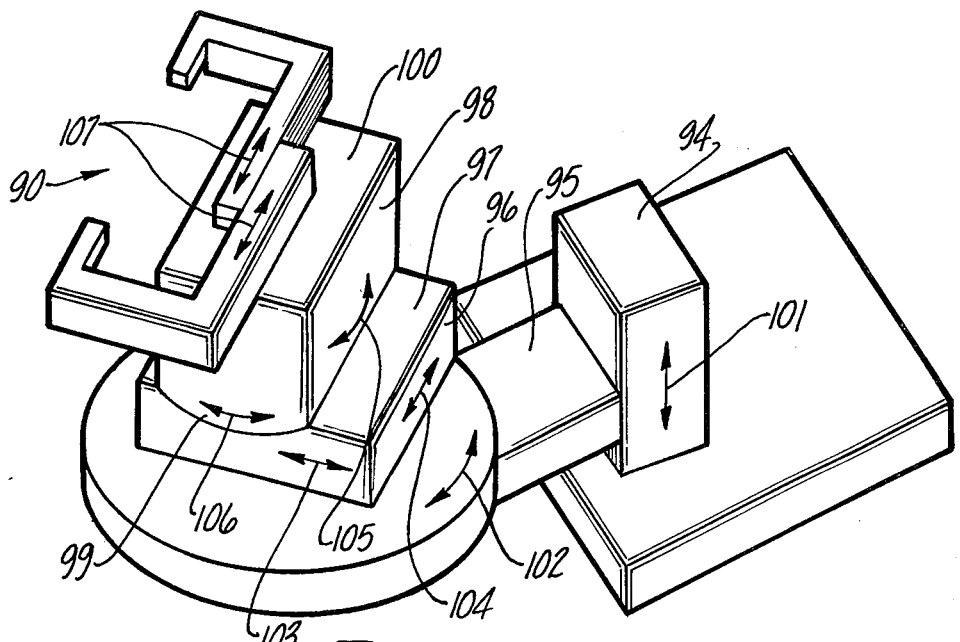
Fig-14
Fig-14A
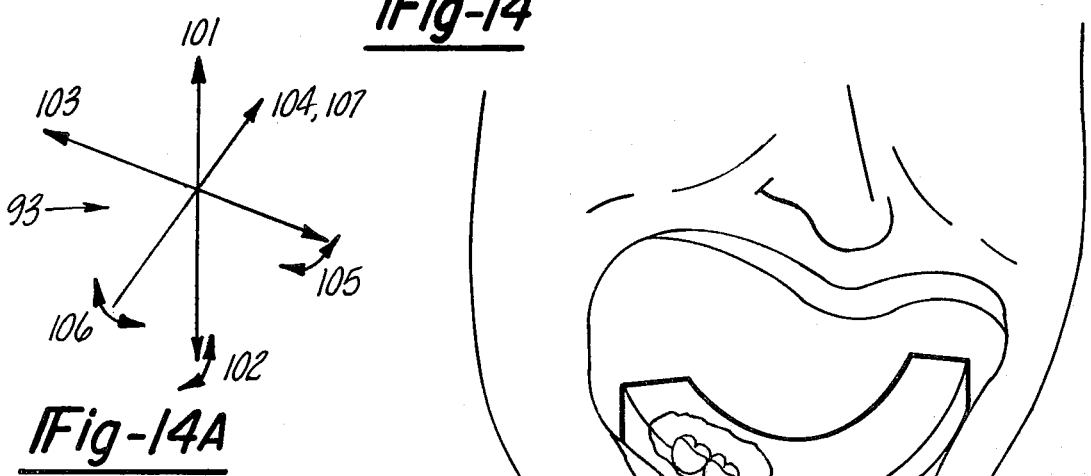
Fig-15
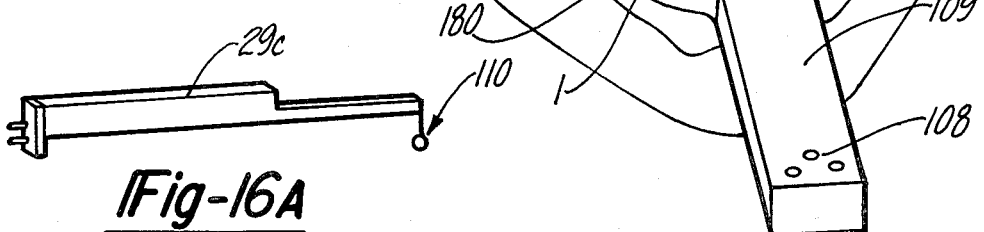
Fig-16A
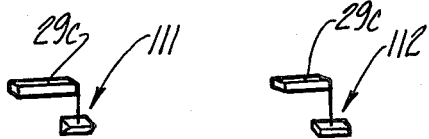
Fig-16B    Fig-16C

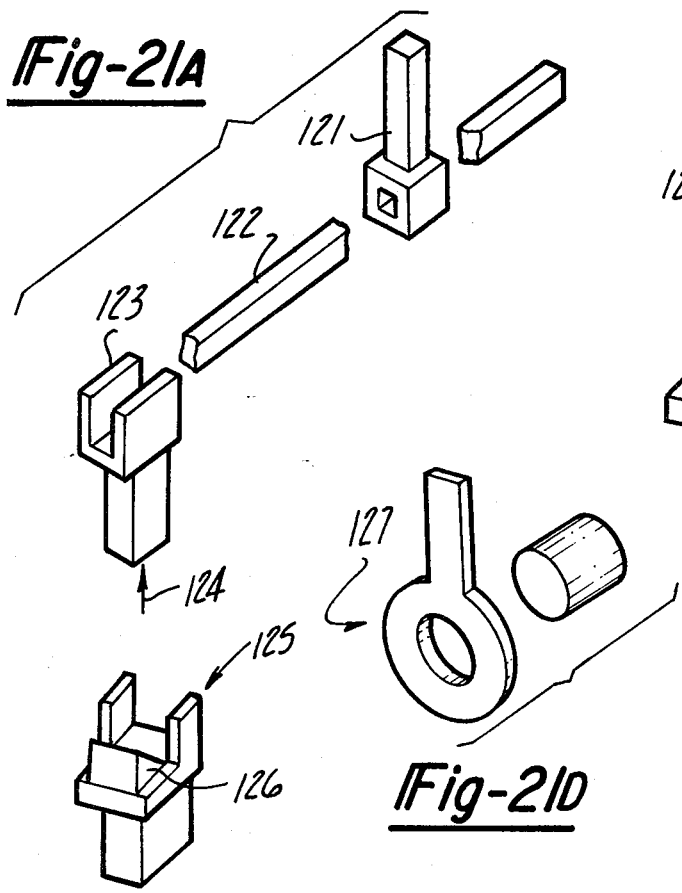
Fig-21A
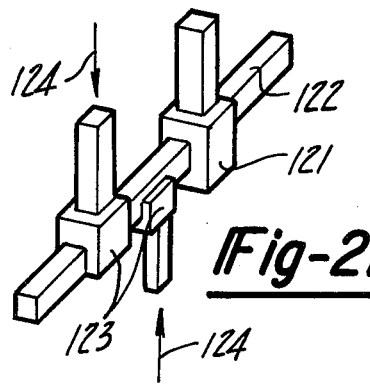
Fig-21B
Fig-21C
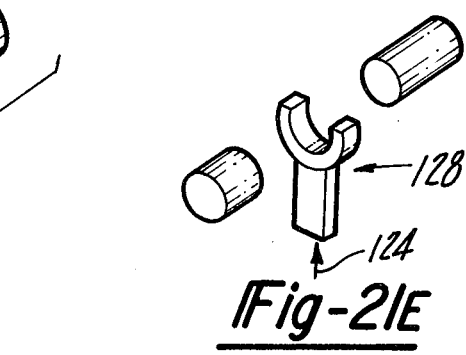
Fig-21D
Fig-21E
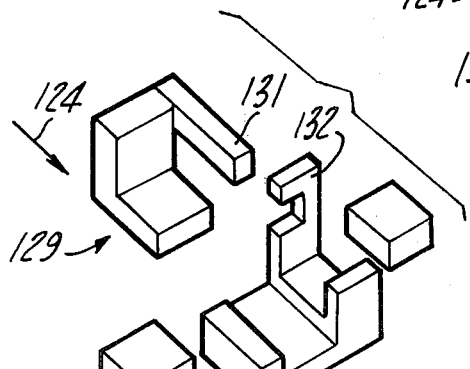
Fig-21F
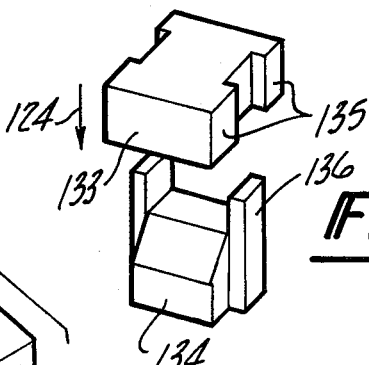
Fig-21G
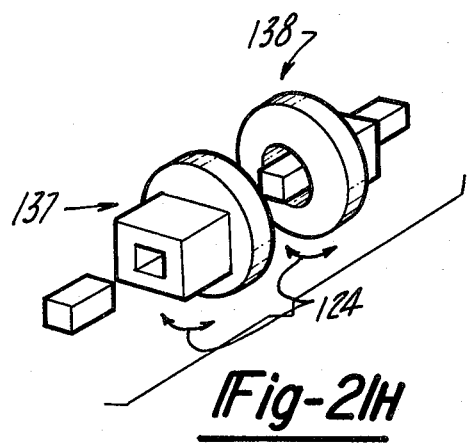
Fig-21H

PROCESS AND APPARATUS FOR TREATING TEETH

FIELD OF THE PRESENT INVENTION

The present invention relates to a process and a device capable of being used by a dental surgeon or by a dental prosthesist for cutting, probing and recording the cartesian topographical coordinates of teeth, dental prostheses, gum and bone tissues, and further relates to therapeutic, orthodontic or periodontal accessories attached to the device. The invention still further relates to a process and device for fabrication by a prosthetist of the corresponding prosthetic or orthopedic constructions mentioned.

BACKGROUND OF THE PRESENT INVENTION

It is known that a dental surgeon frequently has to carry out various operations in the mouth of his patient consisting of cutting, molding or grinding the teeth. The dental surgeon practices this particularly for therapeutic odontological constructions which consist of dental obturations made with the use of amalgam, of gold, of resin, of ceramic or other material, for surgical therapeutic constructions which consist of emplacing implants under the periosteum and splints or intraosseous implants etc., for orthodontic or periodontal therapeutic constructions which consist of emplacing metal or other apparatus aimed at correcting the position of the teeth and for the construction of restorative prostheses such as crowns, bridges, inlay, and onlay or removable prostheses such as dentures and prostheses with mucous support or with corono-mucous insertions.

According to the prior art processes known up until now, prosthetic or therapeutic constructions are machined without provision of guidance for the machining tool or "freehand". Generally, this is started by making an impression in the patient's mouth of the organ or organs to be fitted. From this impression a positive model of the organ is made by molding. The accessories or construction are made on this positive model, either directly by fitting or indirectly by use of a wax model. This model makes it possible to make a mold by the lost wax molding process on which the prosthetist fabricates the final construction. All these operations give rise to a certain number of errors to which the prosthetist must adapt.

Thus, laboratory technicians are expected to have a high level of competence in making the wax model, especially for judging whether the thickness of the wax will be sufficient to withstand the forces developed in use by chewing.

European Pat. No. 0033,492 describes a technique for probing the contours of dental stumps of a plaster model so as to gather data which are subsequently recorded. This permits the prosthetist to refine the shapes and sizes of the prosthesis which he machines with the use of an automatic machine tool. For this purpose it is necessary to add corrections corresponding to the wall thickness to the values read on the plaster stump, but to avoid overcompensating, which would make the prosthesis oversized.

According to another prior art technique taught by Federal German Pat. No. 1,776,012, a plaster model is made immediately after the impression. The impression on the plaster model of the tooth to be crowned is then prepared. A stump is cut, the gingival shoulder of which is worked with great precision. Moreover a cutting guide is provided which makes it possible subsequently to cut the stump of the actual tooth to be crowned according to a profile corresponding to that of the plaster model. Unfortunately, it has been found that this technique does not insure, especially for the gingival shoulder, a sufficient precision of execution.

U.S. Pat. No. 4,182,312 describes a technique for making a detachable prosthesis. In this case the upper and lower dental arches as well as the gum tissues are probed. This makes it possible to record numerical positional values which are used to control an automatic machine for fabricating the prosthesis. Gathering these data requires the use of an apparatus including a guide arm which is connected to a probe arm having three devices for coding the numerical positional values measured in the three dimensions. If it is wished that the numerical values recorded with such a device be significant, the probing must be performed in a very large number of locational points. Moreover the absence of a mechanical pressure sensor interferes with the quality of the numerical values measured.

U.S. Pat. No. 3,861,044 describes a technique for installing an insert or inlay on a tooth. The dental surgeon cuts a cavity on the tooth of his patient in a freehand manner. This cavity is then photographed, measured and coded. From these coded values are derived the data serving for the control of the machine tool for making the inlay. The cut tooth is filled with wax and modeled in the mouth in relation to the original occlusion surface. Finally, this occlusion surface modeled in wax is recorded in the mouth using optoelectronic means. The coded values thus recorded are used to control a machine tool which automatically makes the inlay.

It is seen that none of these prior art processes makes it possible to carry out all of the operations automatically. In all cases an important step is performed manually, so that there is a possibility of errors.

The present invention has the aim of avoiding these disadvantages by achieving a process and a device which is easily used by the dental surgeon, while reducing the likelihood of errors to a greater degree.

SUMMARY OF THE PRESENT INVENTION

The apparatus according to the present invention includes an instrument carrier head on which is fixed the rotary abrasive "air turbine" instrument which the dental surgeon puts into the mouth of his patient. The apparatus is further and it is characterized in that the rotary instrument is provided with detector means delivering signals characteristic of both the movements of the tool and the resistance forces which it encounters. These signals are recorded in a computer with a memory which subsequently is capable of being used to control a machine tool automatically so that the proper probing of the dental surfaces is insured by the surgical tool itself.

The process of the present invention provides for moving a tool carrier in three dimensions in the vicinity of a tooth, measuring the momentary resistances which it encounters, recording and processing in logical units the resistances, and driving a machine tool for machining the prosthesis as directed by the recorded and processed logic units defining the shape and thickness of the prosthesis.

According to another characteristic of the invention the apparatus also includes opticoelectronic and ultrasonic means for probing and recording the contour of the gum and tooth surfaces, especially as regards the unprepared adjacent and antagonistic tooth occlusion surfaces, and calibrated feeler gages for topographically probing and tracking the appliances affixed thereto.

BRIEF DESCRIPTION OF THE DRAWINGS

The attached drawings, given as a non-limiting example, will make it possible to better understand the many objects, features and advantages of the invention.

FIG. 1 is a longitudinal section view of a tooth to be treated;

FIG. 2 is a view similar to FIG. 1 of the tooth after the cutting of a stump thereon;

FIG. 3 is a front elevational view of a prosthesis consisting of a crown to be applied to the stump of FIG. 2;

FIG. 4 is a partially expolded perspective view of an example of an apparatus for treating teeth according to the invention;

FIG. 4a is a schematic view associated with FIG. 4 depicting the logical coordinates used by the apparatus according to the method of the present invention;

FIG. 5 is a partial cutaway enlarged view of of the tool carrier of the apparatus of FIG. 4.

FIG. 6 diagrammatically shows the process of the detection of transverse forces by the tool carrier of FIG. 5 according to the present invention;

FIG. 14 is a perspective view depicting an automatic retaining clamp which, with its different hinged joints and positioning directions is used during the fabrication of a therapeutic construction of the above-mentioned type;

FIG. 14a is a schematic view associated with FIG. 14 illustrating the logical coordinates for the positioning directions used in association with the automatic retaining clamp thereof;

FIG. 15 is a partially cutaway perspective view of a prior art impression tray inserted in a mounth and shows the calibration marks provided on the handle of the impression tray, allowing the cartesian spatial recording of the jaw bones;

FIGS. 16a, 16b, 16c, 17 and 18 are each perspective views showing the various instrumental end elements permitting probing and sounding of the tooth and capable of being mounted in place of the rotary instrument 16;

FIGS. 21a and 21b are perspective views of examples of retaining clamps specific to various operations for the fabrication of prostheses;

DETAILED DESCRIPTION OF THE PREFERRED EMBODIMENT

Figure 7:
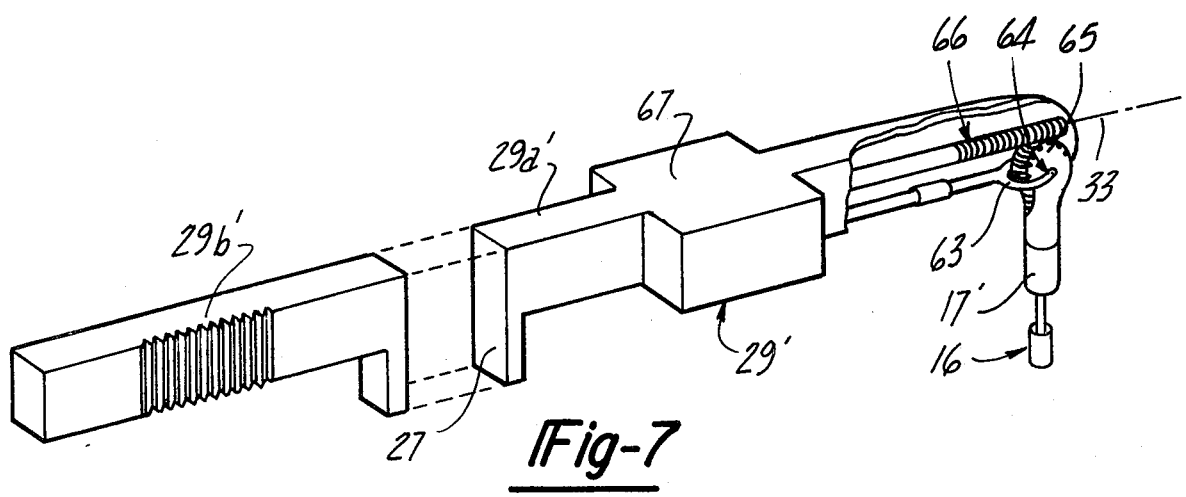
FIGS. 7, 8 and 9 are exploded perspective views showing three other possible modifications for mounting the tool carrier.

Referring now to the drawing, FIG. 1 shows a tooth 1 the volume of which is defined by an occlusion surface 2 and lateral faces 3. At its base, the tooth 1 is surrounded by the dentogingival junction 4. The surface layer consists of the enamel 5 covering the dentin or ivory 6. The roots of the tooth are fixed in the desmondontium 7, the upper part of parodontium of which ensures the junction with the gum at the level of the dentogingival junction 4.

The line 8 drawn in broken lines represents in general the subgingival level of the tooth which corresponds to the prosthesis shoulder.

To treat and crown this tooth, the dentist cuts a crown stump 9, depicted in FIG. 2, which he then covers over with a crown 10 shown in FIG. 3, of metal, a ceramic or other material.

The present invention relates both to the cutting of the sump 9 and to the fabrication of the crown 10 by machining its material. In particular it will be apparent from the following detailed description that the fabrication of the crown 10 leads the prosthetist to define the outer profile 2' and 3' of the prosthesisor crown 10, corresponding to the shape of the occlusion surface 2 and the lateral faces 3 of the tooth 1, the inner profile 11 of the crown 10 intended to mate with the contour 12 of the stump 9 and the exact outline of the lower peripheral shoulder 13 of the crown 10, intended to fit precisely on the gingival shoulder 14 which the dental surgeon has cut around the base of the stump 9.

According to the present invention, and by means of an apparatus 15 shown in FIG. 4, the dental surgeon cuts the stump 9 and the gingival shoulder 14, indicated in FIG. 2, of the tooth 1 by using a rotary tool carrier 17 carrying an abrasive grinder-cutter 16 which can be of any known type or else may correspond to the novel grinders illustrated in FIGS. 26, 28, 29 or 30.

Figure 27:
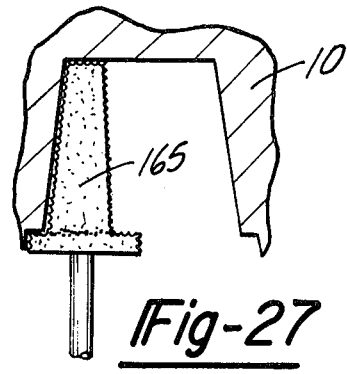
FIG. 27 is a sectional front view of a prosthesis and a corresponding machining tool in the process of machining the prosthesis for affixing to the stump of FIG. 26.
Figures 28, 29, 30, 31, 32:
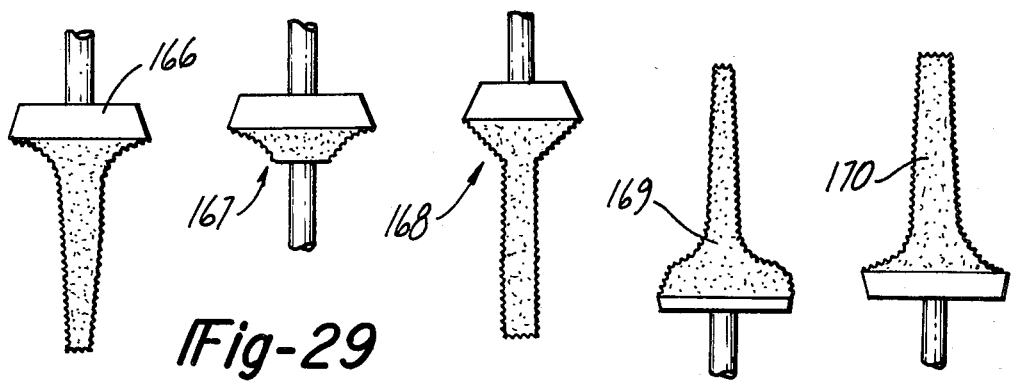
FIGS. 28 to 30 are each front elevational views illustrating a number of modifications of surgical cutters according to the invention.
FIGS. 31 and 32 are front elevational views of alternate surgical cutters and show a number of correspondiong modifications of tools for machining the prosthesis.

On the other hand, for machining the crown 10, the prosthetist uses rotary cutters of the type of those shown in FIGS. 27, 31 or 32.

For carrying out these operations, the present invention provides for making an apparatus 15 of the type illustrated in FIG. 4. For this purpose, the abrasive grinder-cutter 16 is mounted in the rotary tool carrier 17, depicted in FIGS. 4, 5, 7, 8 and 9, for which the invention provides a number of possible mounting variations, shown in FIGS. 4, 7, 8 and 9.

The grinder-cutter 16 is driven in rotation by its spindle 18 inserted in the shaft 19 of the rotor 20. The latter may for example consist of an air turbine rotor 20 of a known type as illustrated in FIG. 5.

According to the present invention the shaft 19 of the rotor has at least two permanent magnets 21 and 22 displaced angularly about the longitudinal axis of the shaft 19 relative to each other. The magnets 21 and 22 are each situated at the level of one of two fixed bearings 23 and 24 of the rotary tool carrier 17. Pickup devices are disposed in each of the bearings 23 and 24. The pickup devices are inductive proximity pickups or those for a magnetic field with the Hall effect, of the type designated schematically in FIG. 6 by the reference number 25. FIG. 6 corresponds to the bearing 23 in the inside of which the magnet 21 rotates, but it is readily apparent that a similar arrangement is provided for the bearing 24 and its associated magnet 22. The magnet 21 is preferably displaced angularly ninety degrees relative to the magnet 22.

When the shaft 19 rotates while the dental surgeon keeps the rotary tool carrier 17 in a mouth adjacent a tooth the tool is subjected by the tooth which it machines to transverse reactions, the direction and intensity of which are detected and measured by the transverse micro-movements resulting from this the motion of the magnets 21 and 22 relative to the inductive and/or Hall-effect proximity pickups inside the bearings 23 and 24.

In a variation of the above described structure wherein the rotor rotates in an air bearing, the rotor itself constitutes the inductive permanent magnet; the inductive proximity pickups, or the Hall-effect pickups, depending on a magnetic field, are distributed around the rotor as shown at 26 in FIG. 5. The bearings 23 and 24 may be built into the very interior of the rotor 20, which reduces the space required for the rotor.

As a result of this arrangement, it is readily apparent that the rotary tool carrier 17 carrying the grinder cutter 16 insures at least two simultaneous functions according to the present invention. First, together with this grinder cutter 16, the rotary tool carrier 17 machines the tooth 1 to cut the stump 9 and the shoulder 14. Simultaneously, the rotary tool carrier plays the part of a sensor continuously reading numerical data characteristic of the profile machined on the stump 9 and the shoulder 14.

The apparatus illustrated in FIGS. 4 to 8 makes it possible to pick up numerical data and store these in a memory, and to retrieve them later for the machining tool when the latter is to be used for cutting the crown 10, as depicted in FIGS. 11, 12, 13, 27, 31 and 32.

In the example of structure illustrated in FIG. 4, the rotary tool carrier 17 is joined fixedly to an arm assembly 29 and an arm portion 29a which is, in turn, connected with an arm portion 29b by a detachable coupling 27. This telescoping arm portion 29b is equipped at its end with a rack 30 which axially crosses a shaft 31.

The shaft 31 is equipped with a stepper motor 32 which by way of a pinion, not represented here, drives the telescoping arm 29b at the level of its rack 30. This telescoping arm assembly 29, in response to the stepper motor, may slide along its longitudinal axis 33 in the direction indicated by the double arrow 34. Moreover the shaft 31 carrying the arm assembly 29 is equipped with a toothed rim 35 and is inserted in a bearing 36 which carries the stepper motor 37.

The stepper motor 37, drives a gear, not shown, which engages the toothed rim 35, and thereby, selectively drives the pivoting of the arm assembly 29 around its longitudinal axis in the direction indicated by the double arrown 38.

Figure 17:
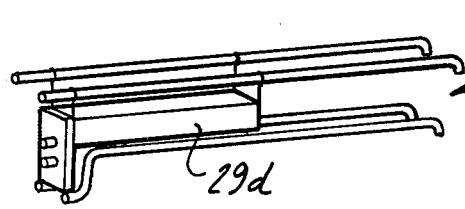
Figure 18:
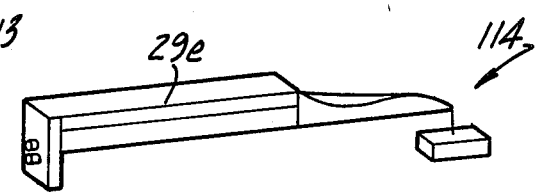

In place of the rotary tool holder carrier 17, an end feeler gage 110, 111 or 112, illustrated in FIGS. 16a through 16c may be mounted at the end of an arm portion 29c which may be mounted to the arm portion 29b by the detachable coupling 27 of the apparatus 15 head. In place of the tool carrier 17 and the feeler gages 110, 111 and 112 an optoelectronic pickup system 113 FIG. 17 may also be mounted to an arm portion 29d which is interconnectable with the coupling 27. Alternatively, a system of an ultrasonic emitter and the pickups 114, depicted in FIG. 18, may be mounted to the arm portion 29e interconnectable with the coupling 27.

Referring again to FIG. 4, the shaft 31 and the arm assembly 29 which have been described above are carried by the bearing 36. The bearing 36 has a leg 39 of which is pivoted on a spindle 40. The spindle 40 is driven by a stepper motor 41 to selectively rotate relative with respect to the bearings 42 in the direction of the double arrow 43. The carrier bearings 42 are fastened to a carriage 44. The latter is subjected to the action of a stepper motor 45 which drives its sliding relative to a supporting plate 46. This sliding is done in a direction 47 perpendicular to the theoretical longitudinal axis 33 of the telescoping arm 29 assembly 29, which motion is denoted by the double arrow 48.

The plate 46 is carried by an elevating column 49 which is capable of being raised or lowered, in the direction indicated by the double arrow 50, in response to a stepper motor 51.

The column 49 and the stepper motor 51 are carried on a platform 53 which is affixed to a gear wheel 54 which pivots about the theoretical axis 52 in the direction indicated by the circular double arrow 55, in response to the driving of a stepper motor 56 which is mounted integrally with a fixed base 57.

The stepper motors 32, 37, 41, 45, 51 and 56 each include an angular data converter of a known type. Each of these devices makes it possible to code and decode the data detected, which makes it possible to transform any movement in one direction or another of the three dimensions shown diagrammatically by the directions 33, 47 and 52 in FIGS. 4 and 4a to generate logic signals, and vice versa.

The fixed base 57 carrying the entire tool carrier apparatus described above is equipped with a fastening leg 58, and is provided with a detachable coupling 59, which can be united with maxillary clamps of any known type.

The base 57 is equipped with a unit for the remote control of the treatment mechanisms, shown here by a console 60. This console 60 may in particular have two control levers 61 and 62.

In the first alternate example of structure illustrated in FIG. 7, the end of the arm portion 29a' of the arm assembly 29' ends in a fork 63 carrying a transverse end spindle 64. On the latter is pivoted a modified circular toothed head 65 of the rotary instrument 17'. A worm gear 66 engages in the toothed circular head 65 which forms a gear driving the pivoting motion of the rotary instrument 17' around the spindle 64. This motion is induced by a stepper motor 67 acting on the angular position of the worm gear 66 about the axis 33 of the arm assembly 29'.

Figure 8:
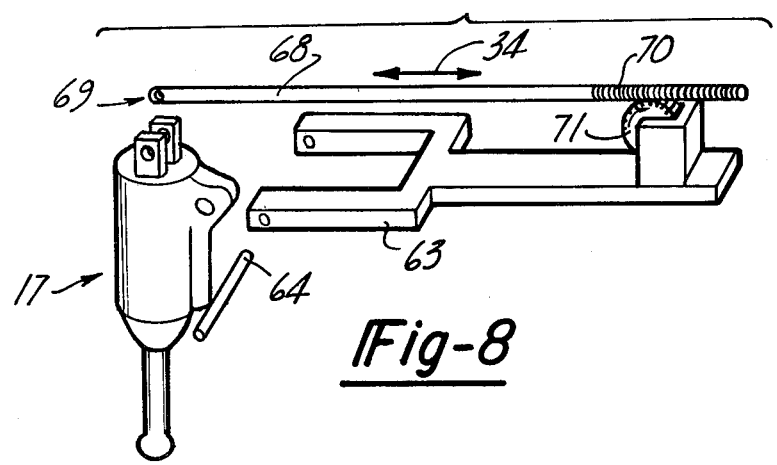

In the second alternate example of structure illustrated in FIG. 8, the rotation of the rotary tool carrier 17 around the transverse spindle 64 carried by the fork 63 is accomplished in response to longitudinal movements, in the direction of the double arrow 34, of a rod 68 having an end pivoted at 69 on the top of the rotary tool carrier 17, while its opposite end has a rack 70 which drives a pinion 71.

Figure 9:
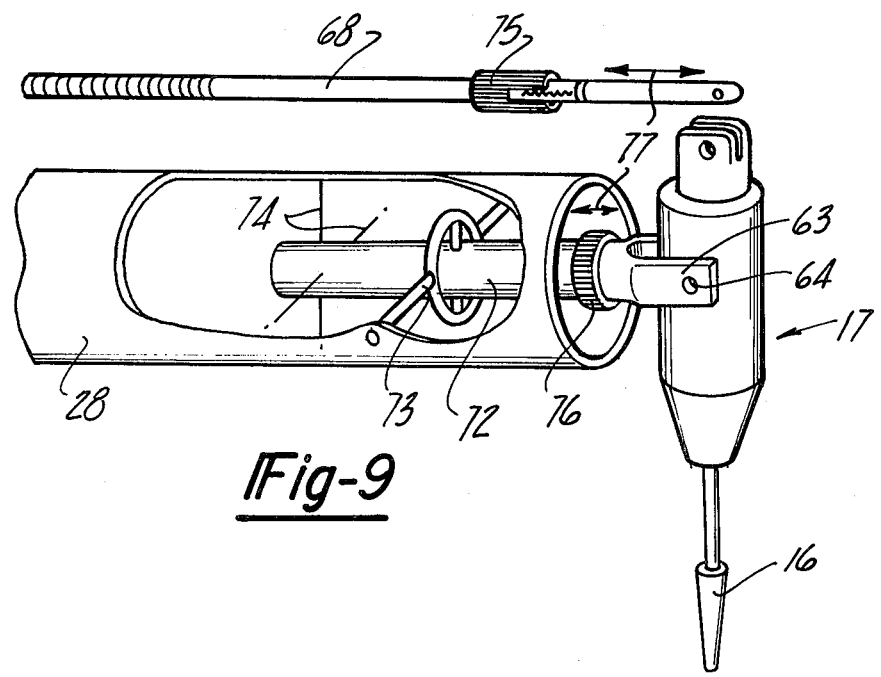

In the third alternate example of structure illustrated in FIG. 9, the rod 72 of the fork 63 is pivotably mounted in a tubular housing 28 which is, in turn, interconnected with the arm assembly 29, not shown in FIG. 9, by appropriate means. The fork 63 is pivotable around two orthogonal axes 74, due to a universal joint 73 interposed the housing 28 and the fork 63.

The movement with two degress of freedom of the free end of the rod 72 makes it possible to record the cutting and probing stresses of the rotary tool carrier 17. The movement in two degrees of freedom resulting from this is driven, as in the previous example, by a sliding rod 68. Mechanical pressure sensors or transducers aree mounted near the free end of the rod 72. Also mounted to the rod 68 and the rod 72 are mechanical pressure sensors or transducers 75 and 76 which make it possible to record the stresses in the direction of the third degree of freedom. A third degree of freedom may be defined in the direction of the arrow 77.

Figure 10:
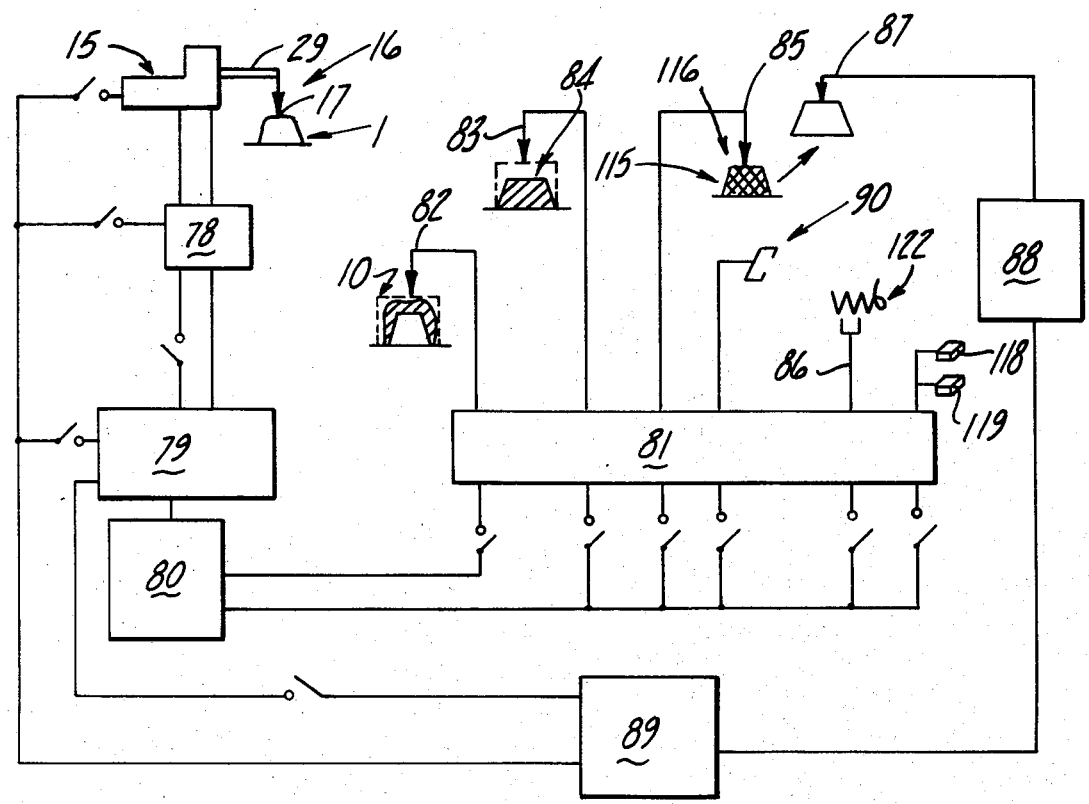
FIG. 10 is a block diagram illustrating the operation of the apparatus according to the invention.

The operation of the above described apparatus is best understood with reference to FIG. 10.

When the dentist works on the tooth 1 with his rotary tool carrier 17 (and grinder-cutter 16) or other instrument coupled with the apparatus 15 shown in FIG. 4, an electronic display unit 78 of the apparatus makes it possible to deliver numeric probing signals which are processed in a data control system 79 and then stored in a memory 80.

Next, by using a machining unit in the form of the machine tool 81, the prosthetist may use the information stored in the memory to direct several subsequent operations, each of which will be described subsequently in greater detail.

Using cutters of a known type with a special shape 164 to 170, depicted in FIGS. 26 to 32, the machine tool 81 can make a tooth crown.

Using the machining tool 82, the machine end 81 can cut the different faces 2', 3', 12 and 13 of a crown 10;

Using the machining tool 83, the machine end 81 can cut a model 84 which, for example, reproduces the stump 9.

Figure 19A:
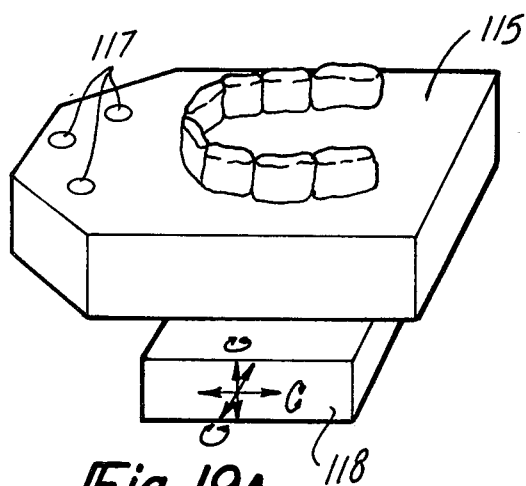
FIGS. 19a and 19b are perspective views respectively showing plaster models of the upper and lower plates.
Figure 19B:
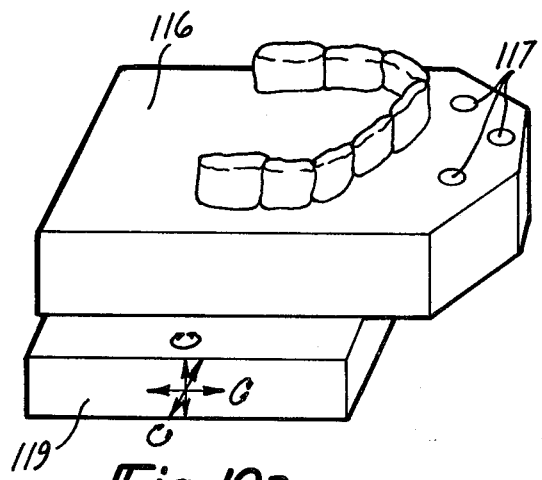
Figure 20:
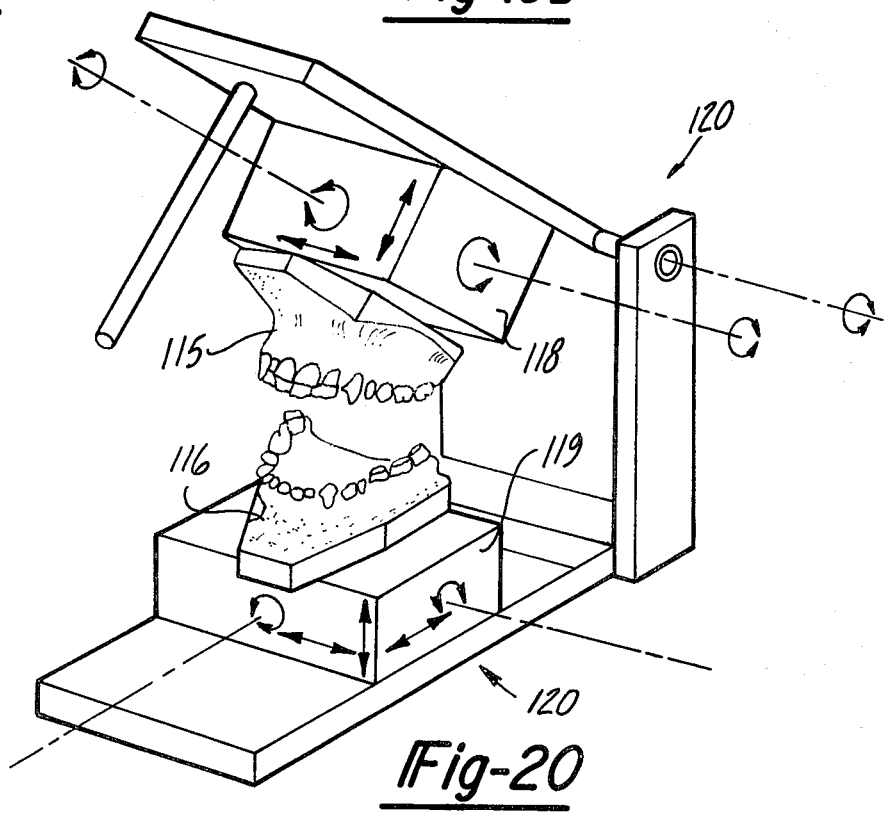
FIG. 20 is a perspective view depicting the automatic mechanical positioning of two plaster models after the step of topographically locating the models according to the present invention and the operational articulating of these models.

Using the machining tool 85, the machine end 81 can retouch and correct the molded duplicates such as the dental arch models 115 and 116, of FIGS. 19a, 19b and 20, respectively.

For these different operations, the prosthetist may use an immobilizing clamp 90, depicted in FIG. 14 with an automated spatial positioning device.

By using machining tools such as retaining clamps or similar appliances, it is possible by bending molding, stamping and boring to permanently or temporarily fasten these appliances to teeth and tissues. Examples include prosthesis clasps, and orthodontic arches and springs.

Using a probing tool 87 provided in an installation 88 connected in parallel with the machining tool 81, the user carries out a probing or scanning operation either of the crown 10 or of the model 84 or of the duplicate (FIG. 10). The machine compares the values thus read with the desired values by means of a memory 89, connected for this purpose to the memory 80.

The cartesian values thus processed and stored in memory serve to modify, if necessary, the buccal cartesian values of the memory 80, or the operating values of the apparatus 15, by modifying the initial cartesian data of the buccal operations, as for example, for the buccal equilibration.

Figure 11:
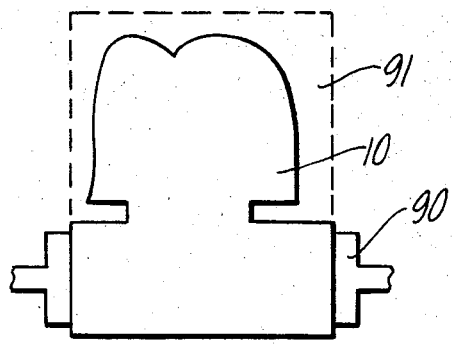
FIGS. 11 and 12 are schematic views and show two successive phases of the fabrication of a dental crown according to the invention.
Figure 12:
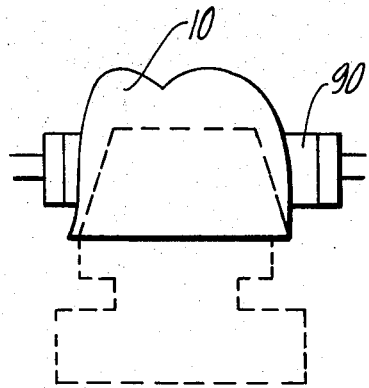

FIGS. 11 and 12 illustrate an example of the the process and apparatus for the machining of a crown 10 starting from a blank part 91 or a part which is already partly preshaped. A clamp 90 of the type illustrated in FIG. 14 holds this blank 91 in place. More particularly, it holds in place the lower part of the blank 91 while the machine tool 81 machines the upper part thereof, as depicted in FIG. 11 and holds in place the upper part while the machine tool 81 machines the lower part, as shown in FIG. 12".

Figure 13:
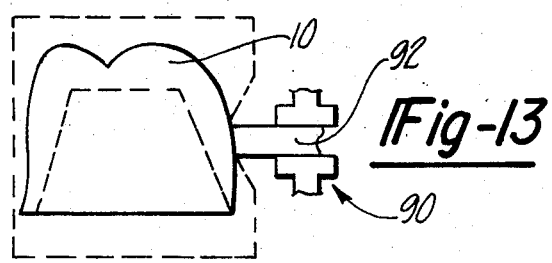
FIG. 13 is a view similar to FIG. 12 and shows an alternate step in the process according to the invention for fabricating a dental crown.

FIG. 13 illustrates another possibility in which the machining is done for all the faces 2', 3', 12 and 13 of the crown 10, both on the inside and the outside, except at the place provided as a temporary fastening foot 92, which is clamped by the clamp 90. This fastening foot is eliminated at the end of the above described operation by an additional machining operation.

In FIG. 14 the clamp 90 is represented diagrammatically. The clamp 90 which permits a spatial positioning of the prosthetic or therapeutic construction in the three directions of space 93, by use of a set of automatic operating units 94, 95, 96, 97, 98, 99, 100. These automatic operationing units make possible movements in each of the directions 101, 102, 103, 104, 105, 106 and 107 shown by by the arrows in FIGS. 14 and 14a.

In FIG. 15 the spatial position of the markings 108 made on the handle of any suitable prior art impression tray 109 are shown. Using one of the instrument tips 110 111, or 112 depicted in FIGS. 16a and 16b these calibration marks are located in cartesian coordinate form relative to the tooth and gum tissues 180 undergoing this impression. The healthy adjacent and antagonistic gum and tooth tissues which are not being treated surgically are themselves probed, either optoelectronically by the tip 113 of FIG. 17, or by the ultrasonic tip 114 of FIG. 18.

In the plaster dental arch models 115 and 116 FIGS. 19a and 19b, respectively, which are drawn from this impression, the relative position of the markings 108 are mechanically reproduced by the machining end 85 FIG. 10 in the markings 117. It is thus possible to locate the plaster models 115 and 116 and their associated appliances relative to the initial markings 108.

In FIGS. 19a and 19b the correct spatial positioning of the two models 115 and 116 corresponding to the arches of the denture is done by the spatial interpositioning of the markings 117 which are brought into relation with them. This positional controlling is satisfactorily accomplished by the automatic positioning ends 118 and 119 of the machining tool 81, not shown in FIGS. 19a and 19b but schematically depicted in FIG. 10. The models 115 and 116 are probed continuously for this purpose by a probing tip 110 of the probing installation 88.

In FIG. 20 the automatic positioning ends 118 and 119 mounted on any suitable kind of articular 120 make possible the dynamic interpositioning of a traditional study and work conforming to the morphology of the patient's jaws.

Of course for all these operations, different types of tools can be used. This may in particular involve cutters 164, 166, 167 and 168 illustrated in FIGS. 26, 28, 29 and 30 respectively, for cutting the teeth.

In the phase of fabricating the prosthesis, tools corresponding to the profile 165, 169 and 170 as illustrated in FIGS. 27, 31 and 32, respectively can likewise be used on the apparatus which is the subject of the present invention.

Moreover different accessories can be used such as restraining clamps, spatial positioners, probes or others.

Thus, FIGS. 21a through 21h show certain examples of retaining clamps specifically for the arches and springs of orthodontics for the bending, shaping and boring end 86 of the machining tool 81. For examples, the element 121 in FIGS. 21a and 21b is an eye into which may be slipped the arch 122, which is subjected by the calibrating clamp 123 to a bending stress in the direction of the arrow 124. The element 125 of FIG. 21a represents a calibrated clamp in the form of a groove and bending wedge 126. The element 127 of FIG. 21d is a clamping eye in a circular shape in which the spring to be shaped slides.

The element 128 of FIG. 21e represents a calibrating clamp having a semicircular groove for bending in the direction of the arrow 124.

The elements 129 and 130 of FIG. 21f, with a simple groove show a clamping and bending unit with interactive keying 131 and 132 prevent slipping.

The elements 133 and 134 of FIG. 21g likewise show a bending clamp having a groove and wedge interlock, with keying between respective portions 135 and 136.

The elements 137 and 138 of FIG. 21h represent a boring clamp unit particularly recommended for angular arches.

Figure 22:
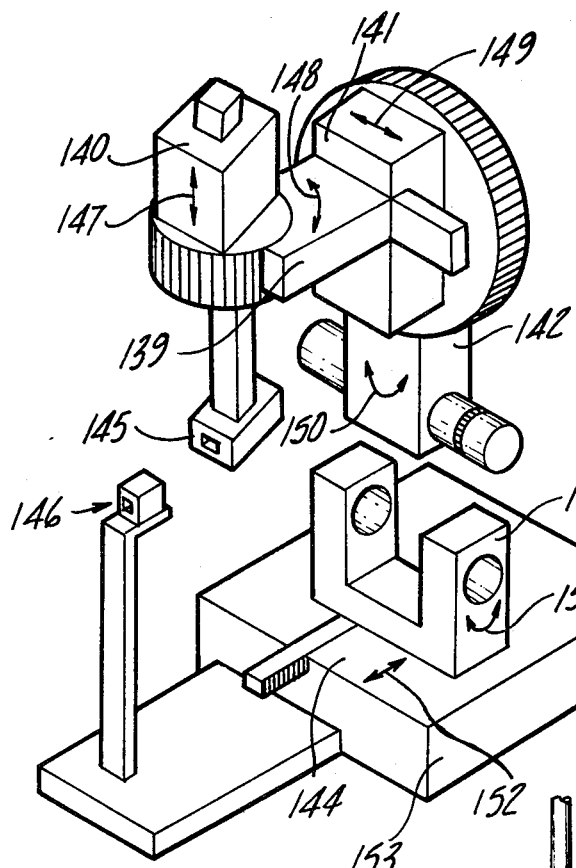
FIG. 22 is a perspective view of an end tool for the machining unit of FIG. 4.

FIG. 22 represents a machining end of the machining unit 81 making it possible to automatically operate the restraining, bending, stamping and boring clamps and elements 121, 123, 125, 127, 128, 129, 130, 133, 134, 137 and 138 described above.

Figure 22A:
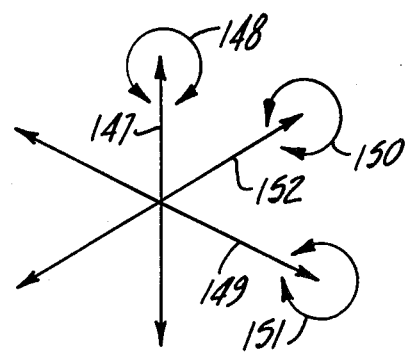
FIG. 22a is a schematic view associated with FIG. 22 illustrating the logical coordinates associated with the end tool thereof.

In using each of the operating units 139, 140, 141, 142, 143 and 144, the clamp 145 may be moved in the three dimensions of space relative to a fixed clamp 146 due to the movements of the machining end in the directions represented by the arrows 147, 148, 149, 150, 151 and 152 of FIGS. 22 and 22a, relative to a fixed base 153.

Figure 23:
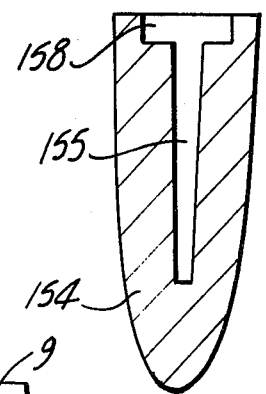
FIG. 23 is a sectional view of a root of a tooth prepared according to the invention.
Figures 24, 25, 26:
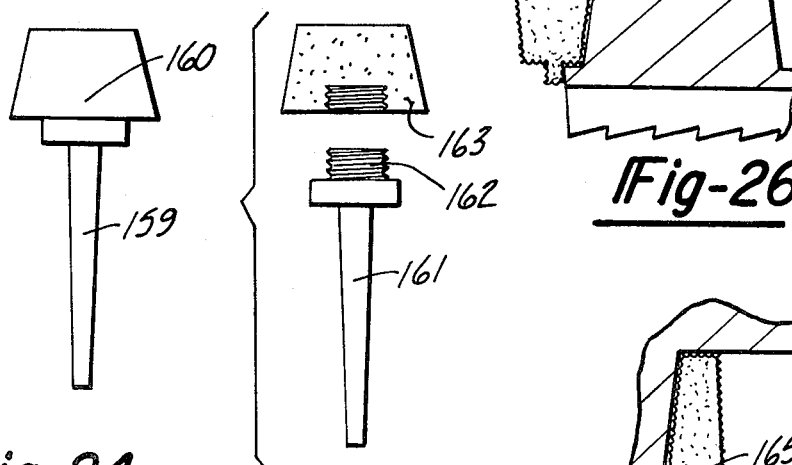
FIG. 24 is a front elevational view of a stump with a pin intended to be implated in the root of FIG. 23.
FIG. 25 is an exploded front elevational view of a screw pin for implantation in the root of FIG. 23.
FIG. 26 is a sectional view through a tooth depicting a surgical tool in the process of cutting a stump, according to the invention.

In the example illustrated in FIGS. 23 to 25, a central channel 155 provided with an upper shoulder 158 is cut in a root 154 for inserting a pin 159 supporting an artificial stump 160 similar to the natural stump 9 previously described.

In the example illustrated in FIG. 25 the dental surgeon first implants a pin 161 provided with a threaded head 162 and subsequently he screws onto the head 162 an internally threaded artificial stump 163.

Figure 35:
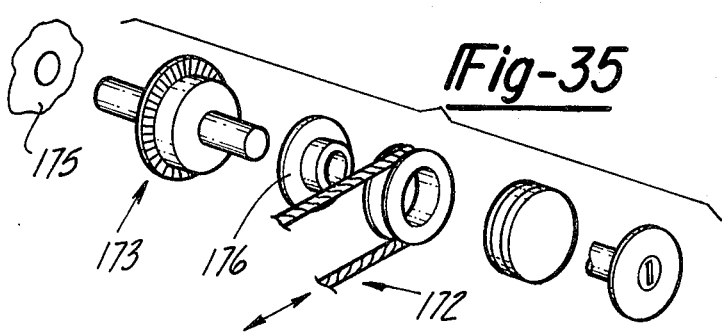

The apparatus of the present invention may be further characterized in that the stepper motors are situated, as shown at 171 in FIG. 3, at a distance from the bearings, plates, and spindles in a machining unit 174, so that they are set in motion by a mechanical cable drive unit 172 which in turn is put into action by each of the stepper motors. At the level of each spindle, bearing, or pivot, an angle recorder 173 makes it possible to read and record the definite position of each spindle or bearing. The machining unit 174 is provided with a clutch 176, best shown in FIG. 35, for each angle recorder which permits the quick withdrawal of the rotary tool carrier out of the mouth of the patient.

One of the advantages of the present invention is to eliminate any danger of error during the probing done in the mouth. In fact, as mentioned hereinabove, the known devices provide for the use of a sensor of which all that is prior art is that its end rests against the teeth already cut, while there is no guarantee that its contact with the tooth occurs solely at one point or even along a complete contact edge. This disadvantage is the source of numerous defects observed in the prior art apparatus.

In the present invention, this defect is automatically eliminated, the sensor consists of the surgical apparatus itself, the cutting edge of which, by definition, is in contact along its whole length with the cut part of the tooth.

Finally, it is seen that the device according to the present invention permits the following additional operations after the initial probing of the occlusion and lateral surfaces of the teeth which have not yet prepared.

The shapes and contours of the abrading, cutting and grinding to be done are determined.

The minimum ideal thickness to be abraded as determined as a function of the mechanical data relating to the materials used in the construction while the mutilation of the tissues is reduced to a minimum.

The anatomical axes relating to each tooth are determined.

The interactive axes and the ideal cutting axis for one or a plurality of teeth between themselves, and the ideal insertion axis of the prosthesis are determined.

A tissue cut is then made which is as precise as possible with complete automation or varying degrees of automation.

By reason of the continuous recording of the movements of the intrabuccal instrument, such as the rotary tool, the pickup, the probe, and the calibrated feeler gage, all of the topographic data is continuously known.

By the use of other instrument tips, the fixed final or temporary appliances at the level of the teeth and tissues are adjusted and positioned.

By adjusting and positioning the calibrated markings on the extrabuccal ends of the maxillary fasteners, the spatial interrelation of these markings to other tooth and gum tissues are recorded, and the spatial interaction of the two jaw bones toward one another is recorded.

Having thus described the present invention by means of a detailed description of the preferred embodiment, given by way of example and not by way of limitation, what is claimed as novel is as follows:

1. An apparatus for treating a tooth comprising:
   a fixed element fixed in a predetermined position relative to said tooth;
   rotary tool holding means movably interconnected with said fixed element;
   probe means interconnected with said rotary tool holding means such as to be driven by said rotary tool holding means to rotate about a predetermined axis;
   detector means interposed said rotary tool holding means and said probe means detecting the resistance force encountered by said probe means as said probe means is moved along the contours of said tooth and generating a first characteristic signal in response to said resistance force;

measuring means measuring the movements of said rotary tool holding means as said probe means is moved along the contours of said tooth and generating a second characteristic signal in response to said movements; and automatic data processing means receiving said first characteristic signal and said second characteristic signal and storing said signals indicative of the shape of said tooth.

2. The apparatus of claim 1 further comprising an automated machining means movable in response to signals generated by said automatic data processing means to machine a predetermined shape in a workpiece.

3. The apparatus of claim 1 further comprising tool carrier means and optoelectronic pickup means interconnected with said tool carrier means for probing and recording the contours of said tooth surfaces, said optoelectronic pickup means generating a third characteristic signal indicative of the contours of said tooth surfaces.

4. The apparatus of claim 1 further comprising ultrasonic transmitter means for probing and recording the shapes and contours of said tooth as well as the adjacent gum and bone tissues, said ultrasonic transmitter means generating a third characteristic signal indicative of said shapes and contours.

5. The apparatus of claim 1 further comprising tool carrier means and non-rotating probe elements comprising feeler gages for probing and locating any therapeutic orthodontic and periodontal prostheses fastened temporarily or permanently to said tooth or adjacent gum tissues.

6. The apparatus of claim 1 wherein said probe means comprises a grinder-cutter such that said tooth is machined to produce a new contour and said first and second characteristic signals are indicative of the newly created contours of said tooth.

7. The apparatus of claim 1 wherein said rotary tool holding means comprises a housing having two spaced apart inductive proximity pickups, shaft means selectively driven to rotate relative to said housing, said probe means being interconnected with said shaft means, and a permanent magnet associated with each of said inductive proximity pickups and angularly displaced relative to each other by a predetermined amount, such that said first characteristic signal is generated by the motion of said shaft means relative to said housing.

8. The apparatus of claim 7 wherein said predetermined amount is ninety degrees.

9. The apparatus of claim 6 wherein said inductive proximity pickups are provided in the bearings of said shaft means.

10. The apparatus of claim 6 wherein said rotary tool holding means comprises an air turbine rotary instrument.

11. The apparatus of claim 6 wherein said probe means comprises a grinding tool axially aligned and interconnected with said shaft means such that said rotary tool holding means drives said grinding tool to alter the contour of said tooth and wherein said first and second characteristic signals are indicative of the newly created contours of said tooth.

12. The apparatus of claim 1 wherein said rotary tool holding means comprises a housing, a rotor comprising a permanent magnet, and a magnetic field pickup distributed around said rotor operating by the Hall-effect to generate said first characteristic signal, said probe means being interconnected so as to rotate with said rotor.

13. The apparatus of claim 6 further comprising interposed said rotary tool holding means and said fixed element:
a circular toothed head on said rotary tool holding means;
arm means extending from said fixed element;
a fork disposed at one end of said arm means, said circular toothed head being mounted to said fork by a spindle;
telescoping arm means interposed said spindle and said fixed element; and
a worm gear engaging said circular toothed head and selectively operable to translate relative thereto to pivot said rotary tool holding means about said spindle.

14. The apparatus of claim 1 further comprising arm means interposed said fixed element and said rotary tool holding means, said arm means comprising selectively operable drive means for pivoting said rotary tool holding means relative to said arm means.

15. The apparatus of claim 14 wherein said rotary tool holding means is interconnected with said arm means by universal joint means such that said rotary tool holding means is movable with two degrees of freedom relative to said arm means and further wherein said arm means further comprises mechanical pressure sensing means generating a characteristic signal in response to pressure resulting from movement of said rotary tool holding means in either of said two degrees of freedom.

16. The apparatus of claim 1 wherein said rotary tool holding means is selectively movable along all three orthogonal axes relative to said fixed element.

17. The apparatus of claim 16 wherein said rotary tool holding means is pivotable about each of said three orthogonal axes such that said rotary tool holding means has freedom of movement in all directions and about all axes.

18. The apparatus of claim 16 wherein movement of said apparatus along each of said three orthogonal axes is selectively controllable by stepping motors.

19. The apparatus of claim 17 wherein rotation of said rotary tool holding means about said three orthogonal axes is selectively controllable by stepper motors.

20. The apparatus of claim 1 further comprising:
interconnecting means interposed said fixed element and said rotary tool holding means permitting freedom of movement of said rotary tool holding means relative to said fixed element along each of said three orthogonal axes;
interconnection means interposed said fixed element and said rotary tool holding means permitting angular motion of said rotary tool holding means relative to said fixed element about each of said three orthogonal axes;
three stepper motors each selectively operable to drive said rotary tool holding means to translate along one of said three orthogonal axes; and
three stepper motors each selectively operable to rotate said rotary tool holding means relative to said fixed element about one of said orthogonal axes.

21. The apparatus of claim 20 wherein each of said stepper motors are situated at a distance from said interconnection means, said apparatus further comprising cable drive means interconnecting each of said stepper motors with one of said interconnection means.

22. The apparatus of claim 20 further comprising angle recorders associated with each of said interconnection means recording the position of each of said interconnection means such as to generate said second characteristic signal.

23. The apparatus of claim 1 further comprising data digitizing means converting said first and second characteristic signals to digital forms and further wherein said automatic data processing means comprises electronic computer means.

24. The apparatus of claim 1 wherein said automatic data processing means processes said first and second characteristic signals to generate a control signal for controlling a machining tool to automatically carve an internal aperture in a prosthetic device for attachment to said tooth.

25. The apparatus of claim 1 wherein said automatic data processing means processes said first and second characteristic signals to generate a control signal for controlling a machining tool to automatically retouch a model of said tooth.

26. The apparatus of claim 1 wherein said automatic data processing means processes said first and second characteristic signals to generate a control signal for controlling a machining tool for automatically producing an orthodontic appliance for interconnection with said tooth.

27. The apparatus of claim 1 wherein said automatic data processing means processes said first and second characteristic signals and generates a control signal for controlling a tool, said tool controlled thereby comprising six stepper motors, three of said stepper motors operating in response to said control signal to move said tool along said three orthogonal axes and three of said stepper motors being selectively operable in response to said control signal to rotate said tool about said three orthogonal axes.

28. A method of preparing orthodontic appliances for a tooth comprising the steps of:
    placing a probing means adjacent said tooth;
    moving said probing means along the surface of said tooth;
    generating a first set of analog signals corresponding to the position of said probing means as said probing means moves along the surfaces of said tooth;
    generating a second analog signal corresponding to the pressure between said probing means and said tooth as said probe means moves along the surfaces of said tooth;
    processing said first set of analog signals and said second analog signal to generate a control signal; and
    transmitting said control signal to an appliance processing device to automatically control the operation of said appliance processing device to prepare said appliance for said tooth.

29. The method of claim 28 wherein said probing means comprises a rotary grinding means such that said rotary guiding means grinds a new surface of said tooth as said probing means is moved therealong such that said first set of analog signals and said second analog signal correspond to said new surface.

30. The method of claim 28 wherein said orthodontic applicance comprises a crown blank, wherein said transmitted signal corresponds to the new external surface of said tooth, and wherein said operation comprises grinding an interior surface in said crown blank corresponding to said new external surface of said tooth such that said crown blank may be fitted to said tooth.

31. The method of claim 28 wherein said processing step further comprises:
    digitizing said first set of analog signals and said second analog signal to produce digital signals;
    processing said digital signals in a computer to produce a digital control signal; and
    converting said digital control signal to an analog control signal.

32. The method of claim 28 wherein said orthodontic appliance comprises a crown blank, wherein said transmitted signal corresponds to the natural exterior surface shape of the tooth and wherein said operation comprises grinding an exterior surface on said crown blank corresponding to said natural exterior surface.

* * * * *

UNITED STATES PATENT AND TRADEMARK OFFICE
CERTIFICATE OF CORRECTION

PATENT NO. : 4,478,580

DATED : October 23, 1984

INVENTOR(S) : Luc P. Barrut

Page 1 of 3

It is certified that error appears in the above-identified patent and that said Letters Patent is hereby corrected as shown below:

Column 3, line 4, after "and" insert ---- includes ----.

Column 3, line 24, delete "of" first occurrence.

Column 4, line 24, delete "diong" and insert ---- ding ----.

Column 4, line 25, after "sis;" insert ---- and ----.

Column 4, line 49, delete "sump 9" and insert ---- stump 9 ----.

Column 5, line 13, delete "20".

Column 5, line 16, after "rotor" insert ---- 20 ----.

Column 5, line 33, after "tooth", first occurrence, insert a comma ---- , ----.

Column 5, line 36, delete "this".

Column 5, line 42, delete "magnet; the" and insert ---- magnet. The ----.

Column 6, line 19, delete "head".

Column 6, line 29, delete "of".

Column 6, line 32, delete "with respect".

Colunn 6, line 38, delete "29".

UNITED STATES PATENT AND TRADEMARK OFFICE
CERTIFICATE OF CORRECTION

PATENT NO. : 4,478,580

DATED : October 23, 1984

INVENTOR(S) : Luc P. Barrut

It is certified that error appears in the above-identified patent and that said Letters Patent is hereby corrected as shown below:

Column 7, line 31, delete "aree" and insert ---- are ----.

Column 7, line 40, delete "(and grinder-cutter 16)" and insert ---- and grinder ----.

Column 7, line 54, delete "tool" and insert ---- end ----. Same line, delete "end" and insert ---- tool ----.

Column 7, line 56, delete "tool" and insert ---- end ----. Same line, delete "end" and insert ---- tool ----.

Column 7, line 59, delete "tool" and insert ---- end ----. Same line, delete "end" and insert ---- tool ----.

Column 8, line 26, delete "Fig. 12"" and insert ---- Fig. 12 ----.

Column 8, line 35, delete "which".

Column 8, line 41, delete "by", first occurrence.

Column 8, line 44, after "110" insert a comma ---- , ----.

Column 9, line 14, after "respectively" insert a comma ---- , ----.

Column 9, line 25, delete "the", first occurrence, and insert ---- a ----.

UNITED STATES PATENT AND TRADEMARK OFFICE
CERTIFICATE OF CORRECTION

PATENT NO. : 4,478,580                                    Page 3 of 3
DATED      : October 23, 1984
INVENTOR(S): Luc P. Barrut It is certified that error appears in the above-identified patent and that said Letters Patent is hereby corrected as shown below:

Column 9, line 26, delete "21a" and insert ---- 21c ----.

Figure 33:
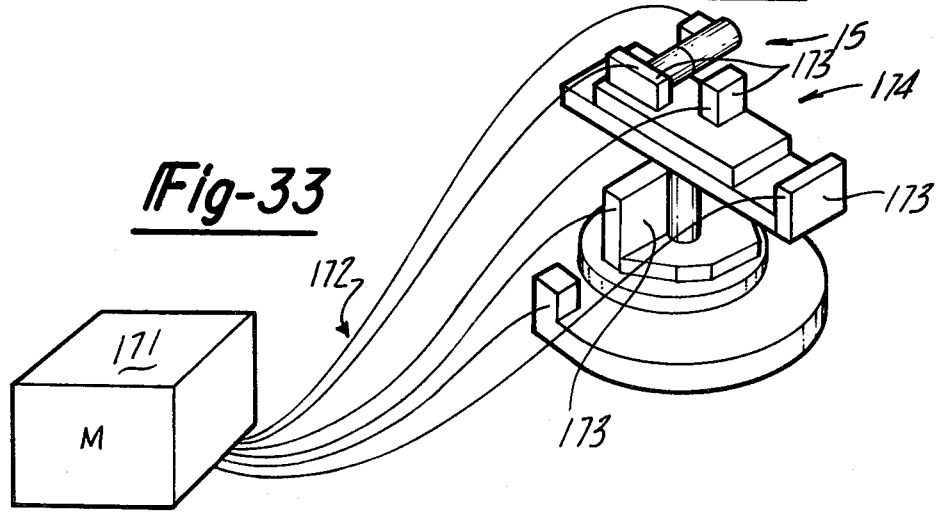
FIGS. 33 to 35 are perspective views and show a modification of the same instrument carrier apparatus operated at a distance by a cable control system.
Figure 34:
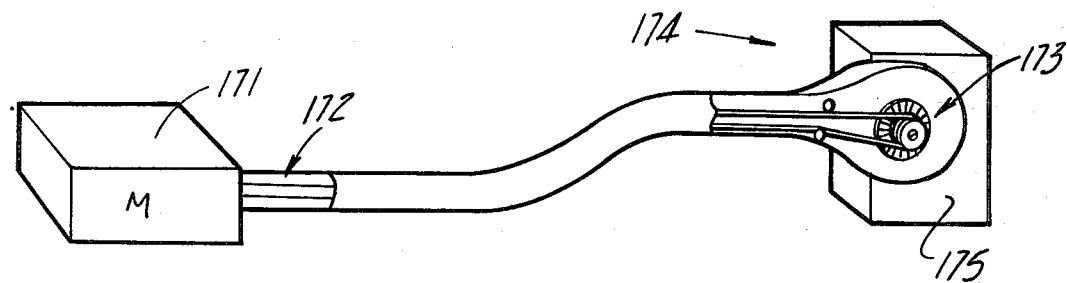

Column 9, line 65, delete "Fig. 3," and insert ---- Fig. 33, ----.

Column 10, line 2, delete "posible" and insert ---- possible ----.

In the Claims

Column 13, line 35, delete "applicance" and insert ---- appliance ----.

Column 14, line 27, delete "applicance" and insert ---- appliance ----.

Signed and Sealed this

Twenty-third Day of July 1985

[SEAL]

Attest:

DONALD J. QUIGG

Attesting Officer        Acting Commissioner of Patents and Trademarks